(12) United States Patent
Mikhail et al.

(10) Patent No.: US 9,408,637 B2
(45) Date of Patent: *Aug. 9, 2016

(54) DEVICE FOR COMPRESSION ACROSS FRACTURES

(71) Applicant: DePuy Synthes Products, Inc., Raynham, MA (US)

(72) Inventors: George Mikhail, West Chester, PA (US); Glen Pierson, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/690,241

(22) Filed: Apr. 17, 2015

(65) Prior Publication Data

US 2015/0216566 A1 Aug. 6, 2015

Related U.S. Application Data

(63) Continuation of application No. 13/693,603, filed on Dec. 4, 2012, now Pat. No. 9,011,501.

(60) Provisional application No. 61/570,527, filed on Dec. 14, 2011.

(51) Int. Cl.
*A61B 17/68* (2006.01)
*A61B 17/84* (2006.01)
*A61B 17/86* (2006.01)
(Continued)

(52) U.S. Cl.
CPC ............ *A61B 17/683* (2013.01); *A61B 17/7055* (2013.01); *A61B 17/846* (2013.01); *A61B 17/8605* (2013.01); *A61B 17/842* (2013.01);
(Continued)

(58) Field of Classification Search
CPC .. A61B 17/86; A61B 17/8605; A61B 17/683; A61B 17/8869
USPC .............. 606/74, 75, 103, 246–279, 300–331
See application file for complete search history.

(56) References Cited

U.S. PATENT DOCUMENTS 4,047,523 A 9/1977 Hall
4,409,974 A 10/1983 Freedland
(Continued)

FOREIGN PATENT DOCUMENTS

CN 101155554 4/2008
CN 101352367 1/2009
(Continued)

*Primary Examiner* — Christopher Beccia
(74) *Attorney, Agent, or Firm* — Fay Kaplun & Marcin, LLP

(57) ABSTRACT

A bone fixation device includes a first element extending from a first head to a first shaft along a first longitudinal axis and having a first channel extending therethrough. The first head rests against a portion of bone adjacent to a first hole through which the first shaft is inserted. A second element includes a second shaft extending along a second longitudinal axis to a second head and having a second channel extending therethrough, the second head resting against a portion of bone adjacent to a second hole through which the second shaft is inserted. The second channel is dimensioned to receive the first shaft therein. A tensioning element is insertable through the first and second channels so that tension applied at a second end thereof imparts a compressive force to the a bone into which the first and second elements are inserted.

15 Claims, 2 Drawing Sheets

(51) Int. Cl.
*A61B 17/70* (2006.01)
*A61B 17/88* (2006.01)

(52) U.S. Cl.
CPC ....... *A61B 17/8869* (2013.01); *A61B 2017/681* (2013.01)

(56) References Cited

U.S. PATENT DOCUMENTS

| | | | |
|---|---|---|---|
| 4,530,114 A | 7/1985 | Tepic | |
| 4,569,338 A | 2/1986 | Edwards | |
| 4,590,928 A | 5/1986 | Hunt et al. | |
| 4,930,499 A | 6/1990 | Rowe | |
| 5,000,165 A | 3/1991 | Watanabe | |
| 5,108,397 A | 4/1992 | White | |
| 5,127,912 A | 7/1992 | Ray et al. | |
| 5,129,904 A | 7/1992 | Illi | |
| 5,152,794 A | 10/1992 | Davidson | |
| 5,300,073 A | 4/1994 | Ray et al. | |
| 5,306,275 A | 4/1994 | Bryan | |
| 5,382,257 A | 1/1995 | Lewis et al. | |
| 5,458,599 A | 10/1995 | Adobbati | |
| 5,515,562 A | 5/1996 | Miller et al. | |
| 5,797,915 A | 8/1998 | Pierson, III et al. | |
| 5,800,544 A | 9/1998 | Demopulos et al. | |
| 5,885,294 A | 3/1999 | Pedlick et al. | |
| 5,899,901 A | 5/1999 | Middleton | |
| 5,989,252 A | 11/1999 | Fumex | |
| 6,010,505 A | 1/2000 | Asche et al. | |
| 6,041,485 A | 3/2000 | Pedlick et al. | |
| 6,080,192 A | 6/2000 | Demopulos et al. | |
| 6,106,556 A | 8/2000 | Demopulos et al. | |
| 6,126,660 A | 10/2000 | Dietz | |
| 6,197,028 B1 | 3/2001 | Ray et al. | |
| 6,197,065 B1 | 3/2001 | Martin et al. | |
| 6,214,004 B1 | 4/2001 | Coker | |
| 6,302,887 B1 | 10/2001 | Spranza et al. | |
| 6,348,053 B1 | 2/2002 | Cachia | |
| 6,368,326 B1 | 4/2002 | Dakin et al. | |
| 6,508,841 B2 | 1/2003 | Martin et al. | |
| 6,520,990 B1 | 2/2003 | Ray | |
| 6,544,267 B1 | 4/2003 | Cole et al. | |
| 6,558,387 B2 | 5/2003 | Errico et al. | |
| 6,565,568 B1 | 5/2003 | Rogozinski | |
| 6,602,214 B2 | 8/2003 | Heinz et al. | |
| 6,613,059 B2 | 9/2003 | Schaller et al. | |
| 6,626,916 B1 | 9/2003 | Yeung et al. | |
| 6,648,890 B2 | 11/2003 | Culbert et al. | |
| 6,648,903 B1 | 11/2003 | Pierson, III | |
| 6,712,855 B2 | 3/2004 | Martin et al. | |
| 6,730,092 B2 | 5/2004 | Songer | |
| 6,761,722 B2 | 7/2004 | Cole et al. | |
| 7,037,308 B2 | 5/2006 | Medoff | |
| 7,153,305 B2 | 12/2006 | Johnson et al. | |
| 7,326,222 B2 | 2/2008 | Dreyfuss et al. | |
| 7,410,489 B2 | 8/2008 | Dakin et al. | |
| 7,651,528 B2 | 1/2010 | Montgomery et al. | |
| 7,704,252 B2 | 4/2010 | Albertson et al. | |
| 7,722,643 B2 | 5/2010 | Schaller et al. | |
| 7,749,255 B2 | 7/2010 | Johnson et al. | |
| 7,771,426 B2 | 8/2010 | Burch et al. | |
| 7,780,707 B2 | 8/2010 | Johnson et al. | |
| 7,789,895 B2 | 9/2010 | Heinz | |
| 7,799,057 B2 | 9/2010 | Hudgins et al. | |
| 7,892,255 B2 | 2/2011 | Schaller et al. | |
| 7,938,832 B2 | 5/2011 | Culbert et al. | |
| 7,947,064 B2 | 5/2011 | Bergeron et al. | |
| 9,011,501 B2 * | 4/2015 | Mikhail | A61B 17/683 606/305 |
| 2003/0236555 A1 * | 12/2003 | Thornes | A61B 17/0401 606/232 |
| 2004/0260297 A1 * | 12/2004 | Padget | A61B 17/683 606/916 |
| 2008/0177306 A1 | 7/2008 | Lamborne et al. | |
| 2009/0228049 A1 | 9/2009 | Park | |
| 2010/0036440 A1 * | 2/2010 | Morris | A61B 17/72 606/320 |
| 2011/0137356 A1 | 6/2011 | Kollmer | |

FOREIGN PATENT DOCUMENTS

| | | |
|---|---|---|
| DE | 20 2007 017159 | 5/2008 |
| EP | 0260222 | 3/1988 |

* cited by examiner

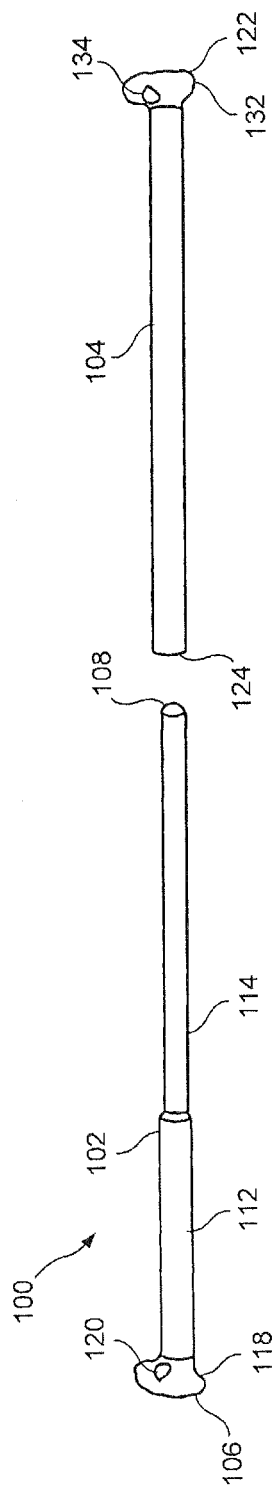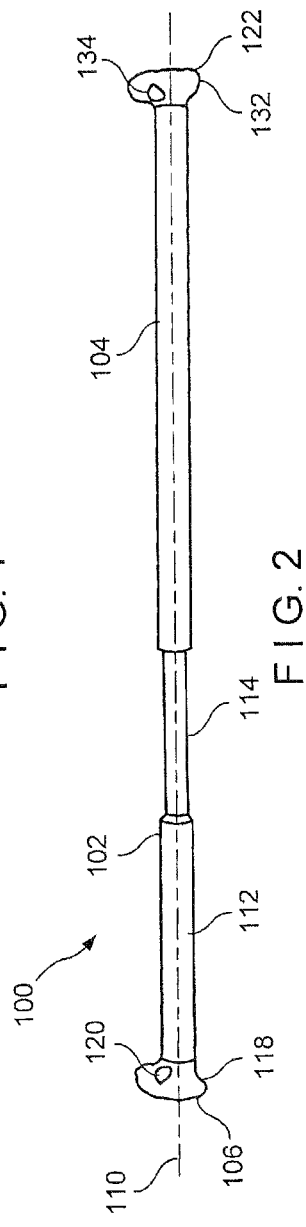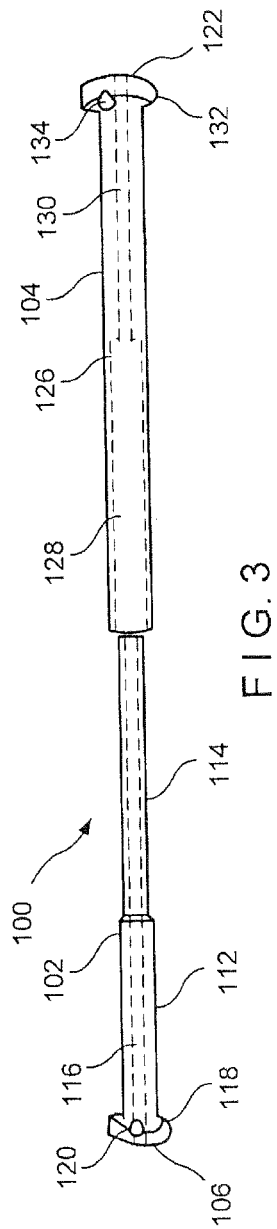

DEVICE FOR COMPRESSION ACROSS FRACTURES

PRIORITY CLAIM

The present application is a Continuation Application of U.S. patent application Ser. No. 13/693,603 filed on Dec. 4, 2012, now U.S. Pat. No. 9,011,501, which claims the priority to U.S. Provisional Patent Application Ser. No. 61/570,527 filed on Dec. 14, 2011. The entire disclosure of these patents/applications are expressly incorporated herein by reference.

BACKGROUND INFORMATION

Fractures of the pelvis and, more specifically, of the sacroiliac joint are often treated by inserting a fixation device across the fracture site. Present fixation systems and methods are generally directed to the insertion of one or more sacral bars or cancellous screws across the fracture site. The sacral bars are formed as elongated planar rods passed through the pelvis posterior to the sacrum until a free, end of the rod extends out of an opposing wall of the pelvis. Threaded nuts are then screwed onto the ends of the sacral bar to create and maintain compression of the pelvis. Cancellous screws can be inserted to span across the pelvis or can be inserted from either side of the pelvis to maintain the stability of the sacroiliac joint. However, these screws rely heavily on an overall strength of the bone and thread purchase to maintain the compression of the pelvis. These devices are therefore susceptible to failure due to loss of bone strength (e.g., due to osteoporosis, etc.), loosening of the threaded bolts and/or a loss of bony purchase (e.g., through rotational and/or longitudinal movement of the sacral bars within the bone).

SUMMARY OF THE INVENTION

The present invention is directed to a bone fixation device comprising a first element extending from a first head at a first end to a first shaft at a second end along a first central longitudinal axis and having a first channel extending therethrough, the first head extending transverse to the first shaft providing a first shoulder which, in an operative configuration, rests against a portion of bone adjacent to a first hole through which the first shaft is inserted to define a maximum extent to which the first element may be inserted into the hole. The bone fixation device also comprises a second element including a second shaft extending along a second central longitudinal axis from a third end to a head at a fourth end thereof and having a second channel extending therethrough, the second head extending transverse to the second shaft providing a second shoulder which, in an operative configuration, rests against a portion of bone adjacent to a second hole through which the second shaft is inserted to define a maximum extent to which the second element may be inserted into the second hole, the second channel being dimensioned to slidably receive the first shaft therein. The bone fixation device also comprises a tensioning element insertable through the first and second channels, the tensioning element including a first end sized to prevent the first end from entering one of the first and second channels so that, tension applied at a second end of the tensioning element imparts a compressive force to the first and second elements and, consequently to a bone into which the first and second elements are inserted.

BRIEF DESCRIPTION OF THE DRAWINGS

FIG. 1 shows a first perspective view of a exemplary bone fixation element according to the present invention in a first configuration;

FIG. 2 shows a perspective view of the bone fixation element of FIG. 1 in a second configuration;

FIG. 3 shows a second perspective view of the bone fixation element of FIG. 1;

DETAILED DESCRIPTION

Figure 4:
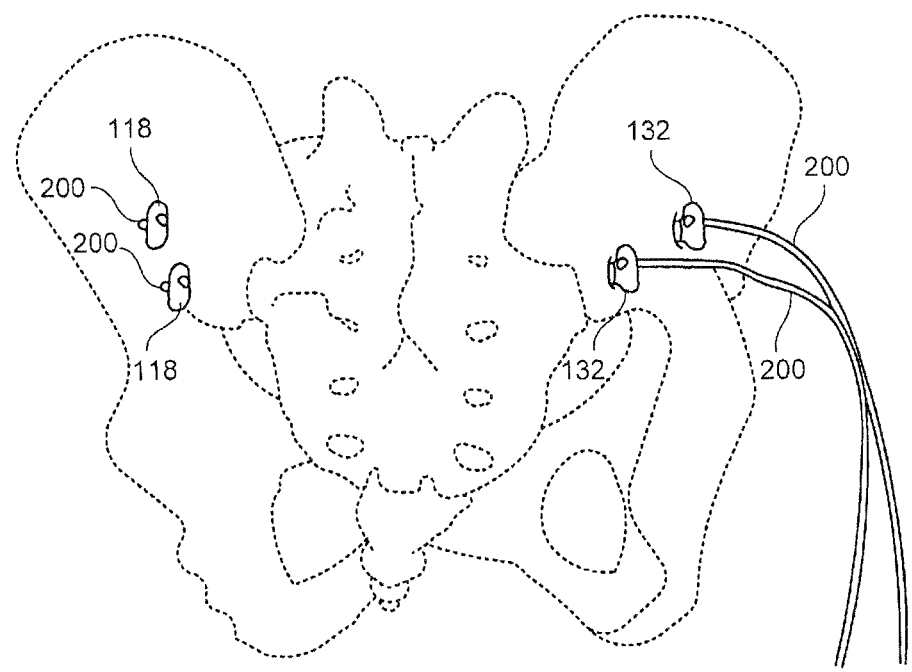
FIG. 4 shows a perspective view of the bone fixation element of FIG. 1 in an implanted configuration.

The present invention may be further understood with reference to the following description and the appended drawings, wherein like elements are referred to with the same reference numerals. The present invention relates generally to devices and methods for the fixation of a fractured or otherwise damaged pelvic bone. Specifically, the present invention relates to methods and devices for inserting a bone fixation element into the bone. The exemplary bone fixation element according to the invention comprises a first elongated element and a second elongated element, each extending along a longitudinal axis. In an operative configuration, the first and second elements are inserted through first and second lateral openings provided on opposing sides of a pelvic bone. In one embodiment, the first and second lateral openings can be two ends of a single hole formed by drilling completely across the pelvis. In another embodiment, two openings may be drilled on opposing walls of the pelvis. A free end of the first element is then inserted into a channel extending through the second element until the first and second elements are securely seated against the pelvic bone. A cable is then inserted through the first and second elements. A first end of the cable comprises a cable stop configured to lockingly engage an opening on a lateral head of the first element. The cable is then locked in position at a lateral end of the second element using a crimp to secure the first and second elements in a desired position relative to one another and compress the fractured bone, as will be described in greater detail later on. It is noted that although the exemplary system and method are discussed with respect to a sacroiliac fixation system and method, the invention may be used in any other bone fixation procedure in any other bone of the body by modifying the dimensions and shape of the apparatus to suit the particular anatomy. The term "medial" as used herein refers to a direction approaching a medial plane of a body in an operative configuration while the term "lateral" refers to a direction extending away from the medial plane in a right and left direction.

Figure 5:
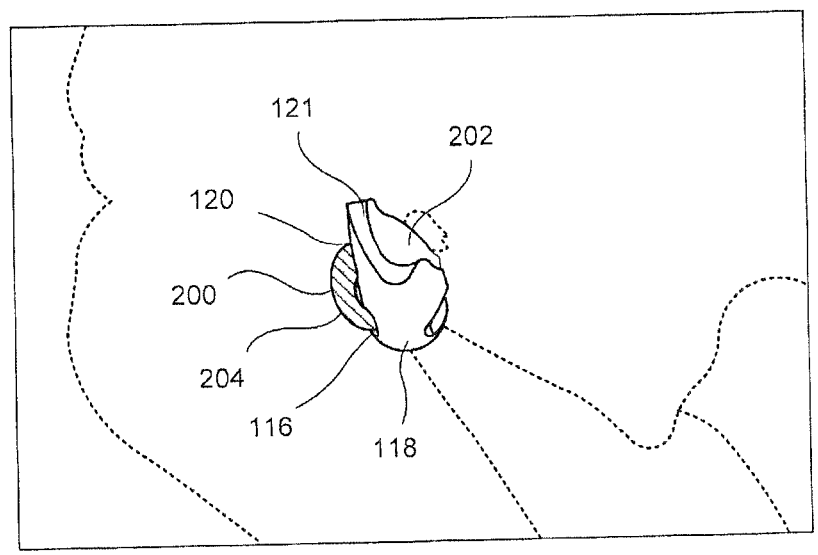
FIG. 5 shows a side view of the bone fixation element of FIG. 1 in an implanted configuration.

As shown in FIGS. 1-5, a bone fixation device 100 according to an exemplary embodiment of the invention comprises a first element 102 and a second element 104. The first element 102 extends from a lateral end 106 to a medial end 108 along a central longitudinal axis 110. The first element 102 according to this embodiment is substantially cylindrical and comprises a lateral body portion 112 having a first outer diameter and a medial body portion 114 having a second outer diameter, the second outer diameter being smaller than the first outer diameter. An elongated first channel 116 extends through the first element 102 from the lateral end 106 to the medial end 108. The first channel 116 is in longitudinal alignment with the longitudinal axis 110 and is configured and dimensioned to receive a cable 200 therethrough, as will be described in greater detail later on. The lateral end 106 comprises an increased diameter head 118 having an oblong cross-sectional shape. It is noted, however, that any other cross-sectional shape (e.g., oval, circular, rectangular, etc.) may be used without deviating from the scope of the invention. The head 118 also comprises an opening 120 extending therethrough, a hole axis of the opening 120 extending substantially parallel to the longitudinal axis 110. In another exemplary embodiment, the hole axis of the opening 120 may extend at any other angle relative to the axis 110. The opening 120 is positioned adjacent to the channel 116. As shown in FIGS. 4-5, the head 118 may also comprise a countersunk portion 121 configured to aid in manipulation of the cable 200, as will also be described in greater detail below.

The second element 104 extends from a lateral end 122 to a medial end 124 along the central longitudinal axis 110. The second element 104 according to this embodiment is substantially cylindrical in shape and comprises a substantially uniform outer diameter which is substantially equivalent to the first outer diameter of the lateral body portion 112. However, those skilled in the art will understand that the first and second elements 102, 104, respectively, may take any desired shape so long as the medial body portion 114 is slidably receivable within an elongated second channel 126 extending through the second element 104. The second channel 126 extends from the lateral end 122 to the medial end 124 in longitudinal alignment with the longitudinal axis 110 and is configured and dimensioned to permit insertion of the medial body portion 114 thereinto. In one exemplary embodiment, the channel 126 has a substantially uniform diameter substantially equivalent to the outer diameter of the medial body portion 114 with a slight clearance to permit the medial body portion 114 to slide therein. In another exemplary embodiment, as shown in FIG. 3, the channel 126 comprises a medial channel portion 128 and a lateral channel portion 130. The medial channel portion 128 has a diameter substantially equivalent to or greater than second outer diameter of the medial body portion 114 and smaller than the first outer diameter of the lateral body portion 112. This configuration permits the insertion of the medial body portion 114 into the channel 126 while preventing the lateral body portion 112 from being inserted therein. In an exemplary embodiment, the first and second portions 102, 104 are dimensioned so that, when inserted to an operative configuration, the medial body portion 114 is seated within the medial channel portion 128 with enough overlap to maintain stability. Varying a length of the overlap allows adjustment of the length of the device 100 to account for variations in anatomy in different patients. In another embodiment, the device 100 may be provided in a variety of lengths so that a physician may select a device having a length range conforming to the requirements of a particular procedure. In a preferred embodiment, the device 100 may be configured to prevent the medial body portion 114 from being fully seated in the medial channel portion 128. That is, by having the medial body portion 114 only partially seated in the medial channel portion 128, a greater amount of compression may be applied via the cable 200, as will be described in greater detail later on. The lateral channel portion 130 has substantially the same diameter as the first channel 116 so that the cable 200 inserted through the device 100 follows a smooth, substantially unobstructed path. The lateral end 122 comprises an increased diameter head 132 having an oblong cross-sectional shape similar to the shape of the head 118. It is noted, however, that the head 132 may comprise any other shape without deviating from the scope of the invention. The head 132 comprises an opening 134 extending therethrough, a hole axis of the opening 134 extending substantially parallel to the longitudinal axis 110. As with the opening 120, the hole axis of the opening 134 may also extend at any angle relative to the axis 110.

In accordance with an exemplary method according to the invention, a physician or other user makes incisions open to the right and left lateral walls of a pelvis. The fracture is then reduced and provisionally stabilized using, for example, Kirschner wires, as those skilled in the art will understand. A drill may then be used to form at least one longitudinal hole through the pelvis. A guide wire may first be inserted in the desired portion of the bone in a target insertion orientation. A cannulated drill may then be guided over the guide wire to open the bone to a desired diameter selected to accommodate the device 100, as those skilled in the art will understand. In an exemplary embodiment, two holes may be drilled through the pelvis across the fracture to receive two devices 100, although any number of holes may be drilled to conform to the requirements of the particular procedure, as those skilled in the art will understand. The cable 200 having the cable stop 202 on a first end thereof is then inserted into the opening 120 of the first element 102. The cable stop 202 may be an enlarged end portion of the cable 200 having a diameter greater than a diameter of the opening 120. In an exemplary embodiment, the cable stop 202 is inserted into the opening 120 from a medial direction so that when the first element 102 is positioned in the bone, the cable stop 202 is positioned toward the bone. As those skilled in the art will understand, this configuration minimizes stresses applied to the cable stop 202 in an operative configuration and helps to prevent loosening of the cable 200 relative to the bone. The first and second elements 102, 104 may then be inserted into the drilled hole from the left and right walls of the pelvis, respectively, until the medial body portion 114 is seated within the medial channel portion 128, as described in greater detail earlier. In this configuration, the heads 118, 132 are in contact with the pelvis and the cable stop 202 is positioned adjacent the bone, as shown in FIG. 3. The cable stop 202 is seated within the concave portion of the head 118 so the head 118 is in direct contact with the bone without interference from the cable stop 202. The free end of the cable 200 (not shown) is then inserted into the channel 116 from the lateral end 106, forming a loop 204 adjacent the head 118. As those skilled in the art will understand, the cable 200 may be configured and dimensioned to minimize a protrusion of the loop 204 out of the head 118 therefore minimizing a profile of the implanted device 100. The loop 204 aids in removal of the device 100 from the body, as will be described in greater detail later on. The cable 200 is guided through the channel 116 and channel 126 until the free end exits the lateral end 122. The free end of the cable 200 is then inserted into the opening 134 from the lateral end. A crimp is then advanced over the free end of the cable 200 and advanced until it contacts the head 132 of the second element 104. The crimp may be any crimp known in the art. A tensioning mechanism threaded over the free end of the cable 200 is then operated as would be understood by those skilled in the art to apply a desired tension to the cable consequently applying a desired compressive force to the bone. The crimp is then crushed in a known manner to maintain the desired tension on the cable and the free portion of the cable 200 extending away from the crimp is trimmed. As would be understood by those skilled in the art, the countersunk portion 121 provides a space for into which the cable cutter may be advanced to allow a cable cutting device to snip the cable close in minimizing the protrusion of the free end of the cable 200.

A physician may decide to remove the device 100 from the body after a predetermined amount of time has elapsed (e.g., once the bone has healed, etc.). To remove the device, a cable cutting mechanism may be used to cut the loop 204, thereby removing the compressive force applied on the bone by the device 100. The device 100 and cable 200 may then be removed from the body.

It will be apparent to those skilled in the art that various other modifications and variations may be made in the structure and the methodology of the present invention, without departing from the spirit or scope of the invention. For example, the exemplary system and method disclosed herein may be used for the treatment of any bone fracture wherein compression is required and opposing ends of the fractured bone are accessible to the physician. For example, the exemplary system and method may be used for the fixation of fractures of a patella, condyle, etc., wherein the compression may be aided by any number of additional bone fixation devices (e.g., intramedullary nail) without deviating from the scope of the invention. Thus, it is intended that the present invention cover modifications and variations of the invention provided that they come within the scope of the appended claims and their equivalents.

What is claimed is:

1. A bone fixation device, comprising:
    a first element including a first head and a first shaft extending along a first central axis from a first end connected to the first head to a second end, the first element including a first channel extending therethrough, the first head extending transverse to the first shaft to provide a first shoulder which, in an operative configuration, rests against a portion of bone adjacent to a first hole through which the first shaft is inserted to define a maximum extent to which the first element may be inserted into the first hole, the first head including a first opening extending therethrough adjacent to the first channel;
    a second element including a second head and a second shaft extending along a second central axis from a first end connected to the second head to a second end, the second element including a second channel extending therethrough, the second head extending transverse to the second shaft to provide a second shoulder which, in an operative configuration, rests against a portion of bone adjacent to a second hole through which the second shaft is inserted to define a maximum extend to which the second element may be inserted into the second hole, the second channel sized and shaped to receive the first shaft therein; and
    a tensioning element insertable through the first opening and through the first and second channels, the tensioning element including a first end sized to prevent the first end from passing through the first opening so that, tension applied at a second end of the tensioning element applies a compressive force to a bone through which the first and second elements are inserted.

2. The device of claim 1, wherein the first opening extends through the first head along an axis substantially parallel to the first central longitudinal axis.

3. The device of claim 1, wherein the first opening extends through the first head at an angle smaller than 90 degrees relative to the first central longitudinal axis.

4. The device of claim 1, wherein the second head includes a second opening extending therethrough adjacent to the second channel, the second opening sized and shaped to permit the second end of the tensioning element to be passed therethrough.

5. The device of claim 4, wherein the second opening extends through the second head along an axis substantially parallel to the second central longitudinal axis.

6. The device of claim 4, wherein the second opening extends through the second head at an angle smaller than 90 degrees relative to the second central longitudinal axis.

7. The device of claim 1, wherein the first head includes a first countersunk portion.

8. The device of claim 1, wherein the second head includes a second countersunk portion.

9. A method for bone fixation, comprising:
    inserting a tensioning element through a first opening extending through a first head of a first element so that an enlarged first end of the tensioning element, which is larger than the first opening, abuts a surface of the first head;
    inserting a first shaft of the first element into a first hole in a bone until the first head rests against a portion of bone adjacent to the first hole, the first shaft extending along a first central axis from a first end connected to the first head to a second end, the first element including a first channel extending therethrough, the first opening extending adjacent to the first channel;
    inserting a second shaft of a second element into a second hole in the bone until a portion of the first shaft is received within a second channel extending through the second element and a second head of the second element rests against a portion of bone adjacent to the second hole, the second shaft extending along a second central axis from a first end connected to the second head to a second head;
    inserting a second end of the tensioning elements through the first and second channels so that the tensioning element forms a first loop adjacent the first head and the second end of the tensioning extends past the second head; and
    applying tension to the tensioning element to provide a compressive force to the bone in which the first and second elements are inserted.

10. The method of claim 9, further comprising inserting the second end of the tensioning element through a second opening extending through the second head adjacent to the second channel so that the tensioning element forms a second loop adjacent the second head.

11. The method of claim 10, further comprising securing the tensioning element to the first and second elements to maintain the compressive force applies to the bone.

12. The method of claim 11, wherein securing the tensioning element includes advancing a crimp over the second end of the tensioning member and crushing the crimp adjacent the second head.

13. The method of claim 9, wherein the enlarged first end of the tensioning element is seated within a concave portion of the first head.

14. The method of claim 9, further comprising cutting a free portion of the tensioning element.

15. The method of claim 11, further comprising removing the compressive force to the bone by cutting one of the first and second loops of the tensioning element.

* * * * *